(12) United States Patent
Habich et al.

(10) Patent No.: US 8,642,090 B2
(45) Date of Patent: Feb. 4, 2014

(54) ADSORBATES CONTAINING ACTIVE SUBSTANCES

(75) Inventors: Andreas Habich, Speyer (DE); York Hartleben, Friedelsheim (DE); Dietmar Weller, Ludwigshafen (DE)

(73) Assignee: BASF SE (DE)

( * ) Notice: Subject to any disclaimer, the term of this patent is extended or adjusted under 35 U.S.C. 154(b) by 1724 days.

(21) Appl. No.: 11/226,994

(22) Filed: Sep. 14, 2005

(65) Prior Publication Data

US 2006/0008533 A1 Jan. 12, 2006

Related U.S. Application Data

(63) Continuation of application No. PCT/EP2004/002244, filed on Mar. 5, 2004.

(30) Foreign Application Priority Data

Mar. 14, 2003 (DE) .................................. 103 11 585

(51) Int. Cl.
*A61K 9/14* (2006.01)
*A01N 37/00* (2006.01)

(52) U.S. Cl.
USPC ............................ 424/489; 424/490; 514/560

(58) Field of Classification Search
None
See application file for complete search history.

(56) References Cited

U.S. PATENT DOCUMENTS

| | | | |
|---|---|---|---|
| 3,247,064 A | 4/1966 | Maekawa et al. | |
| 4,169,069 A * | 9/1979 | Unger et al. | 428/402.24 |
| 4,395,422 A | 7/1983 | Schmidt et al. | |
| 4,434,187 A | 2/1984 | Chandler et al. | |
| 4,533,557 A | 8/1985 | Maruyama et al. | |
| 4,617,294 A | 10/1986 | Krivak et al. | |
| 4,929,774 A | 5/1990 | Fukamachi et al. | |
| 5,133,974 A | 7/1992 | Paradissis et al. | |
| 5,635,214 A | 6/1997 | Ponchon et al. | |
| 5,985,298 A * | 11/1999 | Brieva et al. | 424/401 |
| 6,048,557 A * | 4/2000 | Van Den Burg et al. | 426/99 |
| 6,245,322 B1 | 6/2001 | Simon | |
| 6,368,625 B1 * | 4/2002 | Siebert et al. | 424/466 |
| 2002/0013365 A1 * | 1/2002 | Fimreite | 514/552 |
| 2002/0086062 A1 * | 7/2002 | Kuhrts | 424/499 |
| 2002/0098274 A1 * | 7/2002 | Fimreite et al. | 426/601 |
| 2003/0108580 A1 * | 6/2003 | Hasenzahl et al. | 424/401 |
| 2005/0118208 A1 * | 6/2005 | Bewert et al. | 424/401 |
| 2006/0078618 A1 * | 4/2006 | Constantinides et al. | 424/489 |

FOREIGN PATENT DOCUMENTS

| | | |
|---|---|---|
| DE | 1165574 | 3/1964 |
| DE | 2024051 | 12/1971 |
| EP | 0 062 225 A1 | 6/1985 |
| EP | 0229652 A2 | 7/1987 |
| EP | 0 345 109 A1 | 6/1989 |
| EP | 0 326 026 B1 | 6/1992 |
| EP | 1 036 560 A1 | 9/2000 |
| GB | 962919 | 7/1964 |
| GB | 1333475 | 10/1973 |
| JP | 7-133491 | 5/1995 |
| WO | WO 92/13531 A1 | 8/1992 |
| WO | WO 97/37546 A1 | 10/1997 |
| WO | WO 00/27362 A1 | 5/2000 |

OTHER PUBLICATIONS

Chambin, O., et al., "Dry Adsorbed Emulsion: 1. Characterization of an Intricate Physiochemical Structure" Journal of Pharmaceutical Sciences, (2000), vol. 89, No. 8, pp. 991-999.

* cited by examiner

*Primary Examiner* — Kyle Purdy
(74) *Attorney, Agent, or Firm* — Novak Druce Connolly Bove + Quigg LLP

(57) ABSTRACT

A process is described for producing adsorbates suitable for human or animal nutrition and also cosmetics applications in which a component (A) to be adsorbed is applied to a carrier (C) using at least one stabilizer (B), the mean particle size of the carrier (C) being at least 80 μm, with the proviso that, if the component (A) to be adsorbed is vitamin E, the mixture of (A) and (B) has an HLB value less than 7, and also with the proviso that if the component (A) to be adsorbed is an oil-soluble vitamin and the stabilizer (B) is a glyceride, the freezing point of the mixture of (A) and (B) is below or equal to 80° C. A description is also given of the use of the adsorbates which are thus obtainable.

16 Claims, No Drawings

ADSORBATES CONTAINING ACTIVE SUBSTANCES

RELATED APPLICATIONS

This application is a continuation of International Application No. PCT/EP2004/002244 filed Mar. 5, 2004, which in turn claims priority to German Application No. 103 11 585.4 filed Mar. 14, 2003. The entire contents of each of the foregoing applications are hereby expressly incorporated by reference herein.

Active compound-comprising preparations are of importance in a multiplicity of technical applications, examples are foods, animal foods or cosmetics.

All applications share the problem of providing the respective active compound in an industrially handlable formulation and, at the same time, of not impairing the stability of the active compounds. In the case of the stability of the active compounds, in particular the stability in relatively complex matrices, for example animal feeds, in particular what are termed "premixes", are of great importance. Furthermore, a high loading of the formulations is desirable.

In the prior art, a multiplicity of solutions have been proposed.

U.S. Pat. No. 4,434,187 describes preparations for meat curing which, in addition to the meat-treatment agent, vitamin E, may also comprise lecithin and also silica particles. The silica particles which are suitable according to U.S. Pat. No. 4,434,187 have a mean particle size of from 1.5 to 9 μm.

WO 97/37546 A1 (EP 1 006 806) describes free-flowing preparations which comprise a mixture of fats and, optionally, a filler. The filler mentioned is silica. The preparations described there are physical mixtures of the fats with the filler, and are not adsorbates.

WO 00/27362 A1 (EP 1 133 279) describes dry, free-flowing mixtures of liquid tocopherols which comprise maize starch and silica. The silica used has a particle size of 40-50 μm.

WO 92/13531 A1 (EP 524 308) describes preparations having increased bioavailability of vitamin E, a surfactant emulsifier and at least one inert carrier. The inert carrier mentioned is, inter alia, microcrystalline cellulose, silicon dioxide, starch. The mixtures of vitamin E and surfactant must have an HLB value of from 7 to 14 in order to have the elevated bioavailability required according to the invention.

U.S. Pat. No. 4,617,294 describes free-flowing granular silica particles having a particle size of from 0.14 mm to 0.84 mm and their use as adsorbent for vitamins. The use of stabilizers is not discussed. U.S. Pat. No. 4,617,294, on page 3, lines 44-45, describes the fact that the oil-soluble vitamins can be present in an oil.

EP 0 062 225 B1 (BASF Corp.) describes spray-dried vitamin E powder on a base of hydrolyzed gelatin and caseinates which is produced having from 0.5 to 2.0% by weight of silicon dioxide as spray-drying aid or powdering agent.

EP 0 326 026 B1 (BASF AG) describes vitamin-containing dispersions or emulsions which are converted via customary drying steps into grainy or pulverulent solids. The preparations can comprise anticaking agents, for example silicon dioxide and also fillers, for example starch and silicates.

JP 07-133491 describes solid preparations which comprise an oil-soluble substance. They are obtained by applying liquid oil-soluble compounds to silicates and subsequent solidification. Spherical particles having a particle size of from 20 to 30 μm are used as suitable silicates (Carplex commercial products from Shionogi & Co.). The preparations which are thus obtainable are suitable as low-odor dosage form, in particular for fish oils.

All of the proposed technical solutions are, however, unsatisfactory with respect to the stability of the active compounds, in particular in relatively complex matrices, such as foods and/or animal feeds. In addition, there is the fact that these applications are generally processes which impose particular demands of the handling (good flow properties, low dust, low cohesiveness, low air retention capacity etc.), and also further processability (great metering accuracy, no separation in the mixtures with other constituents). In particular, the formulations should be simple to produce in conventional industrial equipment.

It is an object of the present invention, therefore, to provide active compound-containing formulations which may be handled readily and simultaneously ensure high stability of the active compounds in the preparations. It is an object of the present invention to provide preparations which make it possible to incorporate active compounds into complex substrates, for example into animal feeds or premixes or other mixtures for animal feeds without lump formation occurring or separation occurring or other disadvantages in use or handling, or caking of the substrate, with retention of the stability of the active compound. It is of particular interest here that the remaining constituents of the complex substrate are not affected by the admixture. It is further of importance that the active compounds in the formulations can pass into the rumen.

We have found that this object is achieved by a process for producing adsorbates which are suitable for human or animal nutrition and also cosmetics applications in which a component (A) to be adsorbed, is applied to a carrier (C), using at least one stabilizer (B), the mean particle size of the carrier (C) being at least 80 μm, with the proviso that, if the component (A) to be adsorbed is vitamin E, the mixture of (A) and (B) has an HLB value less than 7, and also with the proviso that, if the component (A) to be adsorbed is an oil-soluble vitamin, and the stabilizer (B) is a glyceride, the freezing point of the mixture of (A) and (B) is below or equal to 80° C.

For the purposes of the present invention, adsorbates are, in particular, preparations in which at least 10% by weight, in particular at least 20% by weight, preferably at least 30% by weight, particularly preferably at least 40% by weight, in particular at least 50% by weight, of the substances to be adsorbed (total of all constituents of the adsorbate without the carrier (C), that is to say customarily at least active compound (A) and stabilizer (B)) are present in the internal pore volume of the carrier (C). The internal pore volume of a carrier can be determined as void volume by the DPB (dibutyl phthalate) method DIN 53601.

Particular preference is given to adsorbates of which at least 60% by weight, preferably at least 70% by weight, in particular at least 80% by weight, is present in the internal pore volume of the carrier (C).

Compared with the preparations described in JP-07-133491, the adsorbates of the present invention are distinguished by better handling and use advantages. In addition, the adsorbates can be produced via conventional fluidized-bed techniques and mixer techniques.

The vitamin-containing preparations described in U.S. Pat. No. 4,617,294 do not contain stabilizers within the meaning of the present invention and do not have increased stability on storage or in complex matrices.

The HLB value (hydrophilic lipophilic balance) is a measure of the oil- and water-solubility of predominantly nonionic surfactants and the stability of emulsions. The HLB value may be determined experimentally by the phenol titration method, in which 5% strength phenol solution is added to the surfactant solution until turbidity develops.

Substances to be Adsorbed (A)

Suitable substances for the component (A) to be adsorbed are in principle all substances which are suitable for human and/or animal consumption. Substances which are suitable in particular are those which are used as active compounds in foods, animal feeds and/or cosmetics.

Suitable components (A) are likewise active compounds in cosmetics, such as vitamins, panthenol, bisabolol, phytosterols, for example cholesterol, perfume oils and/or collagen.

Use can be made of not only water-soluble, water-dispersible compounds, but also oil-soluble compounds. In a preferred embodiment, oil-soluble compounds are used as component (A).

The classification of the components to be adsorbed (A) into oil-soluble substances (for example vitamin E, D, K, A, carotenoids) and water-soluble substances (for example B vitamins, ascorbic acid) is known to those skilled in the art or can be found in the specialist literature. In cases of doubt, the following limitation applies: substances are considered to be oil-soluble as soon as their solubility in water at room temperature (25° C.) falls below 10 mg/kg.

If the component to be adsorbed (A) is an oil-soluble compound, the stabilizer (B) is preferably a stabilizer selected from the group of the glycerides (b-1).

If the component to be adsorbed (A) is an oil-soluble compound, the stabilizer (B) is preferably a stabilizer selected from the group of the polysaccharides (b-3).

If the component to be adsorbed (A) is an oil-soluble compound, the stabilizer (B) is preferably a stabilizer selected from the group of the emulsifiers (b-2).

If the component to be adsorbed (A) is an oil-soluble compound, the stabilizer (B) is preferably a stabilizer selected from the group of the chelators (b-4).

If the component to be adsorbed (A) is an oil-soluble compound, the stabilizer (B) is preferably at least one stabilizer selected from the group of the glycerides (b-1) and at least one stabilizer selected from the group of the emulsifiers (b-2).

If the component to be adsorbed (A) is an oil-soluble compound, the stabilizer (B) is preferably at least one stabilizer selected from the group of the glycerides (b-1) and at least one stabilizer selected from the group of the chelators (b-4).

If the component to be adsorbed (A) is an oil-soluble compound, the stabilizer (B) is preferably at least one stabilizer selected from the group of the chelators (b-4) and at least one stabilizer selected from the group of the emulsifiers (b-2).

If the component to be adsorbed (A) is a water-soluble compound, the stabilizer (B) is preferably a stabilizer selected from the group of the polysaccharides.

If the component to be adsorbed (A) is a water-soluble compound, the stabilizer (B) is preferably a stabilizer selected from the group of the glycerides (b-1).

If the component to be adsorbed (A) is a water-soluble compound, the stabilizer (B) is preferably a stabilizer selected from the group of the emulsifiers (b-2).

If the component to be adsorbed (A) is a water-soluble compound, the stabilizer (B) is preferably a stabilizer selected from the group of the chelators (b-4).

If the component to be adsorbed (A) is a water-soluble compound, the stabilizer (B) is preferably at least one stabilizer selected from the group of the glycerides (b-1) and at least one stabilizer selected from the group of the emulsifiers (b-2).

If the component to be adsorbed (A) is a water-soluble compound, the stabilizer (B) is preferably at least one stabilizer selected from the group of the glycerides (b-1) and at least one stabilizer selected from the group of the chelators (b-4).

If the component to be adsorbed (A) is a water-soluble compound, the stabilizer (B) is preferably at least one stabilizer selected from the group of the chelators (b-4) and at least one stabilizer selected from the group of the emulsifiers (b-2).

In a preferred embodiment, as component (A), compounds are used which are selected from the group consisting of vitamins, carotenoids, xanthophylls, unsaturated fatty acids and lipoic acid.

In a preferred embodiment, the component (A) is at least one vitamin.

Suitable vitamins are not only the water-soluble vitamins, but also the oil-soluble vitamins. Water-soluble vitamins are thiamin ($B_1$), riboflavin ($B_2$), niacin, biotin, vitamin $B_6$ (pyridoxine, pyridoxal, pyridoxamine and also their 5'-phosphate esters), pantothenic acid, folic acid, cobalamin ($B_{12}$) and vitamin C (ascorbic acid and also ascorbyl palmitate).

Oil-soluble vitamins are vitamin A (retinol, retinal, retinoic acid), calciferols (vitamin D), tocopherols (vitamin E), phylloquinone (vitamin $K_1$) and menaquinone (Vitamin $K_2$).

In a preferred embodiment, component (A) is at least one oil-soluble vitamin.

Of course, the vitamins comprise all compounds which exhibit a biological vitamin activity, for instance, for example "vitamin A" comprises all retinoids which qualitatively exhibit the biological activity of all-trans retinol and also its esters, examples are vitamin A acetate, vitamin A propionate, vitamin A palmitate and other esters or derivatives of vitamin A.

Likewise, the term "vitamin E" comprises all derivatives of tocol and tocotrienol which qualitatively exhibit the biological activity of $\alpha$-tocopherol. These include $\alpha$-, $\beta$ and $\gamma$ tocopherol and also $\alpha$-, $\beta$ and $\gamma$ tocotrienol and also the corresponding diastereomers, in particular all-rac-$\alpha$-tocopherol and also the esters, in particular acetates and palmitates.

In a preferred embodiment of the invention, the component (A) to be adsorbed is "vitamin E".

Other suitable components to be adsorbed (A) are carotenoids and xanthophylls, for example lycopene, $\beta$-carotene, $\alpha$-carotene, astaxanthin, astaxanthin esters, canthaxanthin, citranaxanthin, beta-Apo-8'-carotenic acid ethyl ester, beta-Apo-8'-carotenal, lutein and lutein esters, zeaxanthin and zeaxanthin esters, $\beta$-cryptoxanthin and $\beta$-cryptoxanthin esters, capsanthin and capsanthin esters, capsorubin and capsorubin esters, bixin, bixin esters and derivatives thereof, norbixin, norbixin esters and derivatives thereof, crocetin, crocetin esters and derivatives thereof.

Of course, the components to be adsorbed (A) can be present as mixtures of said substances.

Further components to be adsorbed (A) are unsaturated fatty acids and derivatives thereof of the general formula

R—COOH where R is a C1 to C22 alkyl radical, unbranched or branched, containing at least one double bond.

The term "fatty acid" comprises the salts and esters of the respective acids, in particular the alkali metal salts and alkaline earth metal salts and also the methyl, ethyl, n-propyl, isopropyl, n-butyl, isobutyl, sec-butyl and tert-butyl esters.

The unsaturated fatty acids contain one, two, three, four, five or six double bonds in the acyl radical. These include what are termed the isolenic fatty acids, that is to say the double bonds are methylene-interrupted double bonds. Particularly suitable unsaturated fatty acids are what are termed the $\omega$-3, $\omega$-6 and $\omega$-9 fatty acids. Examples of the $\omega$-3 fatty acids are α-linolenic acid, oleic acid, palmitoleic acid and myristoleic acid, of the ω-6 fatty acids, linoleic acid, γ-linolenic acid and arachidonic acid, and of the ω-9 fatty acids, oleic acid, erucic acid and nervonic acid.

Particularly preferably, the unsaturated fatty acids are the polyunsaturated fatty acids containing 22 carbons, the eicosapolyenoic acids.

Particularly preferably, the unsaturated fatty acids are polyunsaturated fatty acids selected from the group consisting of 8,11,14,17-eicosapentaenoic acid (EPA), 5,8,11,14-eicosatetraenoic acid (arachidonic acid=ARA) and docosahexaenoic acid (DHA).

Fatty acids which are also suitable are likewise those having conjugated double bonds, for example α-elaidostearic acid, β-elaidostearic acid or parinaric acid.

In a preferred embodiment of the present invention, the components (A) are polyunsaturated fatty acids, in particular conjugated unsaturated fatty acids.

In a preferred embodiment, the component (A) is at least one conjugated octadecapolyenoic acid, preferably at least one octadecadienoic acid, octadecatrienoic acid or combinations of these octadecapolyenoic acids.

Examples of octadecatrienoic acids are calendic acid or punicic acid.

Particularly preferably, components (A) are conjugated octadecapolyenoic acids where 50% of each fatty acid content is 9-cis-, 11-trans- or 10-trans-, 12-cis-octadecadienoic acids.

Particularly preferably, components (A) are conjugated octadecapolyenoic acids where 60% of each fatty acid content is 9-cis-, 11-trans- or 10-trans-, 12-cis-octadecadienoic acids.

Particularly preferably, components (A) are conjugated octadecapolyenoic acids where less than 5% of the fatty acid content is 11,13-octadecadienoic acid isomers, 8,10-octadecadienoic acid isomers, cis,cis-octadecadienoic acid isomers or trans,trans-octadecadienoic acid isomers or mixtures of these isomers.

Particularly preferably, components (A) are conjugated octadecapolyenoic acids, where less than 3% of the fatty acid content is 11,13-octadecadienoic acid isomers, 8,10-octadecadienoic acid isomers, cis,cis-octadecadienoic acid isomers or trans,trans-octadecadienoic acid isomers or mixtures of these isomers.

Particularly preferably, components (A) are conjugated octadecapolyenoic acids where less than 1% of the fatty acid content is 11,13-octadecadienoic acid isomers, 8,10-octadecadienoic acid isomers, cis,cis-octadecadienoic acid isomers or trans,trans-octadecadienoic acid isomers or mixtures of these isomers.

In a preferred embodiment of the invention, if the components to be adsorbed (A) are unsaturated fatty acids, the stabilizers (B) are at least one compound selected from the class of the chelators (b-4) and at least one compound selected from the class of the emulsifiers (b-2).

Particularly preferably in this case chelators (b-4) are selected from the group consisting of salicylic acid, stearyl citrate, tartaric acid and citric acid.

Particularly preferably in this case emulsifiers (b-2) are selected from the group consisting of addition products of from 15 to 60 mol of ethylene oxide to castor oil and/or hardened castor oil; for example the products obtainable under the trade name Cremophor (BASF AG), polyol esters, and in particular polyglycerol esters, for example polyglycerol polyricinoleate, polyglycerol poly-12-hydroxystearate or polyglycerol dimerate.

Those which are also suitable are mixtures of compounds of a plurality of these classes; and addition products of from 2 to 15 mol of ethylene oxide to castor oil and/or hardened castor oil;

Suitable components to be adsorbed (A) are perfume oils. Perfume oils are mixtures of natural and synthetic fragrances. Natural fragrances are extracts of blossoms (lily, lavender, roses, jasmine, neroli, ylang-ylang), stems and leaves (geranium, patchouli, petitgrain), fruits (aniseed, coriander, cumene, juniper), fruit rinds (bergamot, lemons, oranges), roots (mace, angelica, celeriac, cardamon, costus, iris, calmus), woods (pinewood, sandalwood, guaiac wood, cedarwood, rosewood), herbs and grasses (tarragon, lemongrass, sage, thyme), needles and twigs (spruce, fir, pine, mountain pine), resins and balsams (galbanum, elemi, benzoin, myrrh, olibanum, opoponax). In addition, animal raw materials are used, for example civet and Castoreum. Typical synthetic fragrance compounds are products of the types esters, ethers, aldehydes, ketones, alcohols and hydrocarbons. Fragrance compounds of the ester type are, for example, benzyl acetate, phenoxyethyl isobutyrate, p-tert-butylcyclohexyl acetate, linalyl acetate, dimethylbenzylcarbonyl acetate, phenylethyl acetate, linalyl benzoate, benzyl formate, ethylmethylphenyl glycinate, allyl cyclohexylpropionate, styrallyl propionate and benzyl salicylate. The ethers include, for example, benzyl ethyl ether, the aldehydes, for example, the linear alkanals containing from 8 to 18 carbons, citral, citronellal, citronellyloxyacetaldehyde, cyclamen aldehyde, hydroxycitronellal, lilial and bourgeonal, the ketones, for example, the ionones, α-isomethylions and methyl cedryl ketone, whose alcohols include anethole, citronellol, eugenol, isoeugenol, geraniol, linalool, phenylethyl alcohol and terpireol; the hydrocarbons principally include the terpenes and balsams. However, preference is given to using mixtures of various fragrances which together generate an appealing aroma note. Essential oils of less volatility which are generally used as flavor components are also suitable as perfume oils, for example sage oil, camomile oil, clove oil, lemon balm oil, mint oil, cinnamon leaf oil, lime blossom oil, juniper berry oil, vetiver oil, olibanum oil, galbanum oil, labolanum oil and lavandin oil. Preferably, use is made, alone or in mixtures, of bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, b-damascone, geranium oil bourbon, cyclohexyl salicylate, vertofix coeur, iso-E-super, Fixolide NP, Evernyl, iraldein gamma, phenylacetic acid, geranyl acetate, benzyl acetate, rose oxide, romilat, irotyl and Floramat.

In addition, a suitable component to be adsorbed (A) is lipoic acid, physiologically acceptable derivatives, or salts thereof.

The term "lipoic acid" denotes according to the invention 5-(1,2-dithiolan-3-yl)valeric acid, also called thioctic acid, thioctanoic acid, or thioctan, of the formula I

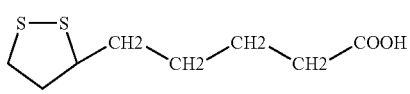

the optical isomers coming under this formula not only as mixtures, for example racemates, but also in pure form, for example R- or S-enantiomers. The preferred isomer is (R)-5-(1,2-dithiolan-3-yl)valeric acid of the formula II

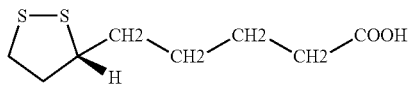

Preference is given to lipoic acid mixtures having an (R)-enantiomeric excess (ee) of at least 40%. Preferably, the (R)-enantiomeric excess is at least 80%, in particular at least 98%.

The enantiomeric excess (ee) is given here from the following formula: ee [%]=(R−S)/(R+S)×100. R and S are the descriptors of the CIP system for the two enantiomers and give the absolute configuration at the asymmetric C(5) atom. The enantiomerically pure compound (ee=100%) is also called a homochiral compound.

Lipoic acid derivatives include, in particular, synthesis precursors and metabolites of lipoic acid, that is to say, primarily, dihydrolipoic acid. Other metabolites are liponamide, lipoyllysine, di-6,8-bisnorlipoic acid and tetranorlipoic acid. Other suitable lipoic acid derivatives are, for example, the esters, thioesters and amides of lipoic acid with amino alcohols, amino thiols and diamines which are described as lipoic acid analogs of the formula (I) in WO 99/45922, which are hereby incorporated by reference in the present application. In accordance with the descriptions of lipoic acid, the respective optical isomers of the derivatives are also included.

The physiologically acceptable salts of lipoic acids and lipoic acid derivatives are, in the present case, preferably base addition salts.

Base addition salts comprise salts with inorganic bases, for example metal hydroxides or metal carbonates of alkali metals, alkaline earth metals or transition metals, or with organic bases, for example ammonia, basic amino acids, such as arginine and lysine, amines, for example methylamine, dimethylamine, trimethylamine, triethylamine, ethylamine, diethylamine, ethylenediamine, ethanolamine, diethanolamine, 1-amino-2-propanol, 3-amino-1-propanol or hexamethylenetetraamine, saturated cyclic amines containing from 4 to 6 ring carbons, such as piperidine, piperazine, pyrrolidine and morpholine, and other organic bases, for example N-methylglucamine, creatine and tromethamine, and also quaternary ammonium compounds, such as tetramethylammonium and the like.

Preference is given to salts with inorganic bases, for example Na, K, Mg, Ca, Zn, Cr and Fe salts.

Stabilizer (B)

Suitable stabilizers are all substances which lead to retarded breakdown of the active compound (A) in the adsorbate. The reference in this case is an adsorbate prepared in the corresponding manner without stabilizer.

If the component to be adsorbed (A) is an oil-soluble compound, the stabilizers (B) are generally selected in such a manner that the mixture of (B) with the components to be adsorbed (A) is solid at temperatures below 80° C., preferably below 60° C., in particular below 40° C.

If the component to be adsorbed (A) is an oil-soluble compound, the stabilizer is preferably at least one compound selected from the group of the glycerides (b-1) and/or the group of the emulsifiers (b-2).

Preferably, (B) is selected in such a manner that the mixture of (B) with the component to be adsorbed (A) is liquid or of low viscosity at the process temperature. The process temperature is the temperature at which the adsorbates are produced. It will be selected by those skilled in the art as a function of the components to be adsorbed and the carrier.

Suitable stabilizers are, in particular, compounds which are selected from the group consisting of b-1) glycerides, b-2) emulsifiers, b-3) polysaccharides and/or b-4) chelators.

Obviously, not only mixtures of compounds from the individual classes of the stabilizers (B) themselves can be used according to the invention, but also mixtures of compounds of different classes. Those skilled in the art select the stabilizer or stabilizer mixtures here as a function of the component to be adsorbed (A).

Particular preference is given to the use of at least one compound of the class of the glycerides b-1) and at least one compound of the class of the emulsifiers b-2).

Preference is given to the use of at least one compound of the class of the glycerides b-1) and at least one compound of the class of the polysaccharides b-3).

Preference is given to the use of at least one compound of the class of the glycerides b-1) and at least one compound of the class of the chelators b-4).

Preference is given to the use of at least one compound of the class of the emulsifiers b-2) and at least one compound of the class of the polysaccharides b-3).

Preference is given to the use of at least one compound of the class of the emulsifiers b-2) and at least one compound of the class of the chelators b-4).

Preference is given to the use of at least one compound of the class polysaccharides b-3) and at least one compound of the class of the chelators b-4).

Particular preference is given to the use of at least one compound of the class of the glycerides b-1), at least one compound of the class of the emulsifiers b-2) and at least one compound of the class of the polysaccharides b-3).

Particular preference is given to the use of at least one compound of the class of the glycerides b-1), at least one compound of the class of the emulsifiers b-2) and at least one compound of the class of the chelators b-4).

Particular preference is given to the use of at least one compound of the class of the emulsifiers b-2), at least one compound of the class of the polysaccharides b-3) and at least one compound of the class of the chelators b-4).

Particular preference is given to the use of at least one compound of the class of the glycerides b-1), at least one compound of the class of the polysaccharides b-3) and at least one compound of the class of the chelators b-4).

b-1 Glycerides

In a preferred embodiment the stabilizer (B) is at least one compound which is selected from the class of the glycerides (b-1).

Preferably, as stabilizers, use is made of at least 2, in particular at least 3, compounds selected from the class of the glycerides (b-1).

The term "glyceride" is taken to mean one glycerol esterified with one, two or three carboxylic residues (mono-, di- or triglyceride). "Glyceride" is also taken to mean a mixture of different glycerides. The glyceride or the glyceride mixture can comprise further additives, for example free fatty acids.

The glyceride used can be a synthetic or naturally occurring glyceride oil or a derivative thereof. "Glyceride" is also taken to mean oils and fats comprising synthetic or naturally occurring fatty acid esters and/or glycerides.

"Glyceride" is also taken to mean derivatives of glycerol. In particular this comprises derivatives in which the fatty acid composition of the naturally occurring non-conjugated or saturated glycerides has not essentially changed.

Preference is given to synthetic or natural glycerides which contain acyl radicals having from 1 to 22 carbons, preferably containing from 12 to 18 carbons. Particular preference is given to natural oils and fats which contain saturated and/or monounsaturated or polyunsaturated acyl radicals containing more than 12, in particular more than 16, carbons and fewer than 22 carbons, preferably from 18 to 20 carbons.

The term "oil" or "fat" is taken to mean a fatty acid mixture which comprises saturated, unsaturated, unbranched and/or branched esterified fatty acid(s). The fatty acids usually contain from 1 to 22 carbons, in particular from 12 to 18, preferably from 12 to 16 carbons.

The oil or fat can comprise various other saturated or unsaturated fatty acids. In particular, depending on the production process, the content of the various fatty acids can vary in the oil or fat. Fatty acid esters are likewise within the scope of the inventive formulation, in particular fatty acid esters which arise during the production of oil from vegetable material. Examples are C1 to C12 alkyl esters of fatty acids. Preferably, the fatty acid esters are present as glyceride, in particular as triglyceride.

Vegetable or animal starting material which can be used is, for example, olive oil, coconut oil, coconut fat, sesame oil, rice germ oil, bamboo oil, bamboo fat, sunflower oil, rapeseed oil, fish oil, soybean oil, palm oil, safflower oil, linseed oil, wheat germ oil, peanut oil, cottonseed oil, corn germ oil, pig fat, beef fat, poultry fat, milk fat, tung oil or shea oil, or a derivative or a mixture thereof. Hydrogenated or partially hydrogenated oils and fats are likewise usable.

The table below summarizes suitable glycerides:

| Glyceride Trade name [manufacturer] | Composition | Melting range | CAS No./ INCI |
|---|---|---|---|
| Shoguwar 41 [Aarhuus Olie] | Hydrogenated soybean oil | approx. 41° C. | |
| Rucawar FH [Aarhuus Olie] | Hydrogenated rapeseed oil | approx. 61° C. | |
| Precirol ATO 5 [Gattefosse] | Mono-, di-, triglycerides of palmitic and stearic acids | approx. 60° C. | 555-44-2 555-43-1 |
| Biogapress Vegetal ATO [Gattefosse] | Esters of palmitic and stearic acids | 60-65° C. | |
| Compritol 888 [Gattefosse] | Mono-, di-, triesters of behenic and arachidonic acids | approx. 75° C. | 94201-62-4 18641-57-1 30233-64-8 |
| Compritol E [Gattefosse] | Mono-, di-, triglycerides of behenic acid | 75-80° C. | 18641-57-1 |
| Vegeol CO-52S [Aarhuus Olie] | Mixture of palmitic acid and stearic acid | 60-65° C. | |
| Palmowar FH [Aarhuus Olie] | Mixture of palmitic acid and stearic acid | 60-65° C. | |
| Colzawar 46 [Aarhuus Olie] | Mixture of palmitic acid and stearic acid | 50-55° C. | |
| Vegeol PR-267 [Aarhuus Olie] | Mixture of Colzawar 46 and Rucawar FH | approx. 70° C. | |
| Vegeol PR-269 [Aarhuus Olie] | Mixture of Vegeol CO-52S and Palmowar FH | 60-65° C. | |
| Cutina CP [Henkel/Cognis] | Synthetic cetyl palmitate | 46-51° C. | 95912-87-1 |
| Edenor NHTi [Cognis] | Hydrogenated beef tallow | 56-61° C. | 67701-27-3 |
| Edenor NHTi V [Cognis] | Vegetable fat of similar C-chain distribution to hydrogenated beef tallow | 57-61° C. | 67701-27-3 |

Emulsifiers b-2

In a preferred embodiment, the stabilizer (B) is at least one compound selected from 5 the class of the emulsifiers (b-2).

Preferably, as stabilizers, use is made of at least 2, in particular at least 3, compounds selected from the class of the emulsifiers (b-2).

In principle, all emulsifiers are suitable which are suitable for foods, animal nutrition and/or cosmetics applications.

Emulsifiers which can be used are, for example, non-ionogenic surfactants from at least one of the following groups:

(1) Addition products of from 2 to 30 mol of ethylene oxide and/or from 0 to 5 mol of propylene oxide to linear fatty alcohols containing from 8 to 22 carbons, to fatty acids containing from 12 to 22 carbons and to alkylphenols containing from 8 to 15 carbons in the alkyl group;

(2) $C_{12/18}$-fatty acid monoesters and diesters of addition products of from 1 to 30 mol of ethylene oxide to glycerol;

(3) Glycerol monoesters and diesters and sorbitan monoesters and diesters of saturated and unsaturated fatty acids containing from 6 to 22 carbons and their ethylene oxide addition products;

(4) Alkyl monoglycosides and oligoglycosides containing from 8 to 22 carbons in the alkyl radical and ethoxylated analogs thereof;

(5) Addition products of from 15 to 60 mol of ethylene oxide to castor oil and/or hardened castor oil; for example the products obtainable under the trade name Cremophor (BASF AG);

(6) Polyol esters, and in particular polyglycerol esters, for example polyglycerol polyricinoleate, polyglycerol poly-12-hydroxystearate or polyglycerol dimerate. Mixtures of compounds of a plurality of these classes of substances are likewise suitable;

(7) Addition products of from 2 to 15 mol of ethylene oxide to castor oil and/or hardened castor oil;

(8) Partial esters based on unbranched, branched, unsaturated or saturated $C_{6/22}$-fatty acids, ricinoleic acid and also 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and also polyglucosides (for example cellulose);

(9) Mono-, di- and trialkyl phosphates and also mono-, di- and/or tri-PEG-alkyl phosphates and salts thereof;

(10) Lanolin alcohols;

(11) Polysiloxane-polyalkyl-polyether copolymers and corresponding derivatives;

(12) Mixed esters of pentaerythritol, fatty acids, citric acid and fatty alcohol as under DE-C 1165574 and/or mixed esters of fatty acids containing from 6 to 22 carbons, methylglycose and polyols, preferably glycerol or polyglycerol and also

(13) polyalkylene glycols.

The addition products of ethylene oxide and/or of propylene oxide to fatty alcohols, fatty acids, alkylphenols, glycerol mono- and diesters and also sorbitan monoesters and diesters of fatty acids or to castor oil are known products available commercially. These are mixtures of homologues, the mean degree of alkoxylation of which corresponds to the ratio of the amounts of substance of ethylene oxide and/or propylene oxide and substrate with which the addition reaction is carried out. $C_{12/18}$-fatty acid mono- and diesters of addition products of ethylene oxide to glycerol are disclosed by DE-C 2024051 as oil-replacement materials for cosmetics preparations. $C_{8/18}$-alkyl mono- and oligoglycosides, their preparation and use are known from the prior art. They are prepared, in particular, by reacting glucose or oligosaccharides with primary alcohols containing from 8 to 18 carbons. As regards the glycoside ester, not only monoglycosides in which a cyclic sugar radical is glycosidically bound to the fatty alcohol but also oligomeric glycosides having a degree of oligomerization preferably up to about 8 are suitable. The degree of oligomerization is a statistical mean which is based on an underlying homologue distribution customary for such industrial products.

Furthermore, zwitterionic surfactants can be used as emulsifiers. The name zwitterionic surfactants is used for those surface-active compounds which bear at least one quaternary ammonium group and at least one carboxylate group and one sulfonate group in the molecule. Particularly suitable zwitterionic surfactants are what are termed betaines, such as N-alkyl-N,N-dimethylammonium glycinates, for example coconut alkyldimethylammonium glycinate, N-acylaminopropyl-N,N-dimethylammonium glycinates, for example cocoacylaminopropyldimethylammonium glycinate, and 2-alkyl-3-carboxylmethyl-3-hydroxyethylimidazolines each containing from 8 to 18 carbons in the alkyl or acyl group, and also cocoacylaminoethylhydroxyethylcarboxymethyl glycinate. Particular preference is given to the fatty amide derivative known under the CTFA name cocamidopropyl betaine. Emulsifiers which are likewise suitable are ampholytic surfactants. Ampholytic surfactants are taken to mean those surface-active compounds which, apart from containing one $C_{8/18}$-alkyl group or $C_{8/18}$-acyl group in the molecule, contain at least one free amino group and at least one —COOH group or —$SO_3H$ group and are able to form internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each containing from about 8 to 18 carbons in the alkyl group. Particularly preferred ampholytic surfactants are N-cocoalkylaminopropionate, cocoacylaminoethylaminopropionate and $C_{12/18}$-acylsarcosine. In addition to the ampholytic surfactants, quaternary emulsifiers can also be used, with particular preference being given to those of the ester quat type, preferably methylquaternized difatty acid triethanolamine ester salts.

In addition, emulsifiers which can be used are glycerophospholipids and glyceroglycolipids. Preference here is given to glycerophospholipids such as lecithin (phosphatidylcholine), cardiolipin, phosphatidylglycerol; phosphatidylserine and alkylacylglycerophospholipids such as plasmalogen.

A combination of all emulsifiers which are suitable, in particular for cosmetics applications, is found in the Handbook of Cosmetic Ingredients of the CTFA (Cosmetic, Toiletry and Fragrance Association) and "emulsifiers" and in the online CTFA database (www.ctfa.org).

Those which are suitable in particular are the diacylglycerides and mixtures thereof known as food emulsifiers, for example the food emulsifiers E 472a, E 472b, E 472e or E 442. In addition, those which are suitable are all emulsifiers mentioned in "Emulgatoren für Lebensmittel" [Emulsifiers for foods] edited by G. Schuster, Springer Verlag 1985, on pp. 55 to 190. Of these, those which are particularly suitable are the emulsifiers mentioned in table 1 (pp. 57-60).

Preference is given to emulsifiers having the EEC Nos. E 322 lecithins, E432 polyoxyethylene (20) sorbitan monolaurates, E433 polyoxyethylene (20) sorbitan monooleate, E434 polyoxyethylene (20) sorbitan monopalmitate, E435 polyoxyethylene (20) sorbitan monostearate, E436 polyoxyethylene (20) sorbitan monotristearate, E 470, E 471 mono- and diglycerides of fatty acids, E 472a, E 472b, E 472c, E472d, E 472e, E 473 sucrose esters of fatty acids, E 474, E 475, E476, E 477, E 481, E 482 calcium stearoyl-2-lactylate, E 483 stearyl tartrate, and also E 493, E 494, E 495, E491, E492 and E 498.

The table below summarizes particularly suitable emulsifiers

| Emulsifier Trade name [Manufacturer] | Characterization |
|---|---|
| Metarin FM [Degussa] | Soybean lecithin Mixture of nonpolar triglycerides and polar phospho- and glycolipids - vegetable oil, emulsifier E 322 |
| Cremophor WO 7 [BASF] | Hydrogenated castor oil, ethoxylated CAS - No. 61788-85-0 INCI Name: PEG-7 Hydrogenated Castor Oil |
| Cremophor CO 40 [BASF] | Hydrogenated castor oil, ethoxylated CAS - No. 61788-85-0 INCI Name: PEG-40 Hydrogenated Castor Oil |
| Imwitor 600 [Condea Chemie] | Polyglycerol polyricinoleate (PGPR) Emulsifier E 476 |
| Grinsted PGPR 90 [Danisco] | Polyglycerol polyricinoleate (PGPR) Emulsifier E 476 |
| Emulan A [BASF AG] | Oleic acid ethoxylate CAS No. 9004-96-0 |
| Cremophor GO 32 [BASF Corp.] | Polyglyceryl-3 oleate CAS No. 9007-48-1 (Generic) 33940-98-6 |
| Cremophor GS 32 [BASF Corp.] | Polyglyceryl-3 distearate CAS No. 9009-32-9 (Generic) 94423-19-5 |
| Lutensol TO 8 [BASF AG] | $C_{13}$-Oxoalcoholethoxylates CAS No. 69011-36-5 |
| Plantacare E 6000 [Cognis] | Caprylyl/capryl glucosides |
| Pluronic ™ PE [BASF AG] | PO/EO block polymers |

Particular preference is given to addition products of from 2 to 30 mol of ethylene oxide and/or from 0 to 5 mol of propylene oxide to unbranched fatty alcohols containing from 8 to 22 carbons, to fatty acids containing from 12 to 22 carbons and to alkylphenols containing from 8 to 15 carbons in the alkyl group.

Particular preference is given to EO/PO block polymers, as can be obtained, for example, under the trade name Pluronic™ PE (BASFAktiengesellschaft).

Particular preference is given to addition products of from 2 to 15 mol of ethylene oxide to castor oil and/or hardened castor oil, as can be obtained, for example, under the INCI name PEG-7 Hydrogenated Castor Oil.

Particular preference is given to addition products of from 15 to 60 mol of ethylene oxide to castor oil and/or hardened castor oil; like products obtainable, for example, under the INCI name PEG-40 Hydrogenated Castor Oil.

Particularly suitable emulsifiers are polyol esters and, in particular, polyglycerol esters, for example polyglycerol polyricinoleate, polyglycerol poly-12-hydroxystearate or polyglycerol dimerate, as can be obtained under the INCI names Polyglyceryl-3-Distearate or Polyglyceryl-3 Oleate. Mixtures of compounds of a plurality of these classes of substance are likewise suitable.

In a preferred embodiment of the invention, the stabilizers (B) are at least one compound of the class of the chelators (b-4) and at least one compound of the class of the emulsifiers (b-2).

b-3) Polysaccharides

In a preferred embodiment, the stabilizer (B) is at least one compound selected from the class of the polysaccharides (b-3).

Preferably, the stabilizers used are at least 2, in particular at least 3, compounds selected from the class of the polysaccharides (b-3).

If polysaccharides are used as carrier C), the stabilizers (B) used are polysaccharides different from (C).

Polysaccharides (synonym glycans) is the collective name for macromolecular carbohydrates, the molecule of which consists of a large number (at least >10, preferably >20, in particular >50) of monosaccharide molecules (glycose) which are glycosidically linked to one another.

Examples of polysaccharides are the homoglycans starch, glycogen, guaran, amylopectin and also cellulose, amylose, dextran and tunicin (polyglucosans, glucans), inulin as polycondensate of D-fructose (polyfructosan, fructan), chitin, alginic acid.

Polysaccharides which are also suitable are heteropolysaccharides (heteroglycans) of different types of monomer units. Known heteroglycans are pectins, mannans, galactans, xylans and other polyoses, and in addition chondroitin sulfates, heparin, hyaluronic acid and other glycosaminoglycans.

Suitable polysaccharides are, for example, maltodextrins, as are commercially available under the name N-Zorbit M (maltodextrins from tapioca starch, National Starch).

Suitable polysaccharides are furthermore starch derivatives, for example such as starch octenyl succinate, commercially available under the name HI-CAP 100, from National Starch.

b-4) Chelators

In a preferred embodiment, the stabilizer (B) is at least one compound selected from the class of the chelators (b-4).

Preferably, use is made, as stabilizers, of at least 2, in particular at least 3, compounds selected from the class of the chelators (b-4).

Suitable chelators are in principle all compounds authorized as chelators for foods and animal feeds. Examples are: Na, K, Ca salts of acetic acid, citric acid and also the Na, K, Ca salts of citric acid, citric acid monoisopropyl ester, monoglyceride esters, triethyl ester and monostearyl ester of citric acid, EDTA, Na, K, Ca salts of EDTA, Na, K, Ca salts of gluconic acid, oxystearin, orthophosphoric acid and also the Na, K, Ca salts of orthophosphoric acid, Na salt of pyrophosphoric acid, Na salt of triphosphoric acid, Na and Ca salts of hexametaphosphoric acid, Ca salt of phytic acid, sorbitol, tartaric acid, salicylic acid, and the Na salt of thiosulfuric acid.

Chelators which are suitable in particular are tartaric acid, salicylic acid, and monostearyl ester of citric acid.

Suitable chelators are described in Thomas E. Furia, "Sequestrants in Food" CRC Handbook of Food Additives, 2nd edition, Volume I, CRC Press, Boca Raton, ISBN 0-8493-0542-X, Chapter 6, pp. 271-280. Chelators which are suitable in particular are the chelators mentioned there on pp. 275-277.

In a preferred embodiment of the invention, the weight ratio of stabilizer (B) to components to be adsorbed (A) is less than or equal to 10, in particular less than or equal to 5, in particular less than or equal to 1, in particular less than or equal to 0.8, in particular less than or equal to 0.5, preferably less than or equal to 0.3.

If the stabilizer (B) is selected from the group of the glycerides (b-1) and/or polysaccharides (b-3), preferably a weight ratio of stabilizer (B) to components to be adsorbed (A) is less than or equal to 10, in particular less than or equal to 5, in particular less than or equal to 1, in particular less than or equal to 0.8.

If the stabilizer (B) is selected from the group of the emulsifiers (b-2) and/or chelators (b-4), preferably a weight ratio of stabilizer (B) to components to be adsorbed (A) is less than or equal to 0.8, particularly less than or equal to 0.5, in particular less than or equal to 0.3, preferably less than or equal to 0.1.

Carrier (C)

Suitable substances for carriers (C) are all substances which are present with a mean particle size of at least 80 µm and can adsorb the active compound or active compounds (A) and the stabilizer or stabilizers (B). Suitable carriers are, in particular, low-molecular-weight inorganic salts, kieselguhr, silica and silica derivatives, sugars, dextrins, starch products and cellulose preparations.

The carrier (C) must not display any adverse interactions with the components used in the inventive formulation and must be harmless for use as an aid in the respective uses, for example in foods, food supplements, animal feeds and cosmetics preparations.

Examples of suitable carriers are: low-molecular-weight inorganic or organic compounds and high-molecular-weight organic compounds of natural or synthetic origin. Examples of suitable low-molecular-weight inorganic carriers are salts, such as sodium chloride, calcium carbonate, sodium sulfate and magnesium sulfate, kieselguhr and silica or silica derivatives, for example silicon dioxide, silicates or silica gels. Examples of suitable organic carriers are, in particular, sugars, for example glucose, fructose, sucrose and also dextrins and starch products.

In addition, suitable carriers C) are the polysaccharides specified under b-3. If polysaccharides are used as carrier C), it is preferred that the stabilizers B) used are polysaccharides which are different from C), in particular, it is preferred that the stabilizers B) used are not polysaccharides.

Examples of high-molecular-weight organic carriers are: starch and cellulose preparations, such as in particular corn starch, corn cob meal, ground rice husks, wheat semolina or cereal flours, for example wheat, rye, barley and oat flour or wheat, rye, barley and oat bran or mixtures thereof.

Particular preference as carrier (C) is given to silicas and silica derivatives, for example silicon dioxides, silicates or silica gels having a mean particle size of at least 80 µm and also mixtures thereof. Such products are commercially available, for example Sipernat® 22 or Sipernat® 2200 (Degussa); Tixosil® 38 X or Tixosil® 68 (Rhodia) or Zeofree 5170 (Huber).

Particular preference is given to hydrophilic silicas.

The present invention also encompasses the presence of mixtures of said carriers.

The mean particle size of the carrier (C) of at least 80 µm, preferably at least 100 µm, preferably at least 200 µm, in particular at least 300 µm, preferably at least 400 µm, is essential to the invention.

In a preferred embodiment the carriers used have a mean particle size less than 1000 µm, in particular less than 800 µm.

The mean particle size here is reported as a [D4,3] value. This can be determined on a Mastersizer S from Malvern Instruments Ltd, Serial Number 32734-08. To describe the width of the particle size distribution, D(v,0.1), D(v,0.5) and D(v,0.9) were determined and also the mean particle size of the distribution [D4,3] reported.

The mean particle size [D4,3] is specified in accordance with the Mastersizer Reference Handbook, Preliminary Manual Chapter 2, pages 22-23, Malvern Instruments Ltd for the Mastersizer S Serial No. 32734-08, Certificate No P 1261, May 1995. [D4,3] is described as "the volume weighted mean diameter".

The mean particle sizes [D4,3] thus determined are, for example, for Sipernat® 22: 136 μm, Sipernat® 2200:364 μm, Tixosil® 38 X:265 μm, Tixosil® 68:302 μm or Zeofree 5170: 287 μm.

The carrier (C) can be present in the inventive formulation at a content of greater than 10% by weight, in particular greater than 20% by weight, preferably greater than 30% by weight, based on the total weight of the adsorbate. Customarily, the carrier is present in a range from 10 to 85% by weight, preferably from about 20 to 85% by weight, based on the total weight of the adsorbate. These values are based on the uncoated stabilized adsorbate.

Coating materials D)

In a preferred embodiment of the invention, the adsorbate is coated. Suitable coating materials are:
a) polyalkylene glycols, in particular polyethylene glycols, of a number-average molecular weight of from about 400 to 15 000, for example from 400 to 10 000;
b) polyalkylene oxide polymers or polyalkylene oxide copolymers of a number-average molecular weight of from about 4000 to 20 000, in particular block copolymers of polyoxyethylene and polyoxypropylene;
c) substituted polystyrenes, maleic acid derivatives and styrene-maleic acid copolymers;
d) polyvinylpyrrolidones of a number-average molecular weight of from about 7000 to 1 000 000;
e) vinylpyrrolidone/vinyl acetate copolymers of a number-average molecular weight of from about 30 000 to 100 000;
f) polyvinyl alcohol of a number-average molecular weight of from about 10 000 to 200 000, polyvinyl phthalate;
g) hydroxypropylmethyl cellulose of a number-average molecular weight of from about 6000 to 80 000;
h) alkyl(meth)acrylate polymers and copolymers of a number-average molecular weight of from about 100 000 to 1 000 000, in particular ethyl acrylate/methyl methacrylate copolymers and methacrylate/ethyl acrylate copolymers;
i) polyvinyl acetate of a number-average molecular weight of from about 250 000 to 700 000, unstabilized or stabilized with polyvinyl pyrrolidone;
j) polyalkylenes, in particular polyethylenes;
k) phenoxyacetic acid-formaldehyde resin;
l) cellulose derivatives, such as ethyl cellulose, ethyl methyl cellulose, methyl cellulose, hydroxypropyl cellulose, hydroxypropyl methyl cellulose, carboxymethyl cellulose, cellulose acetate phthalate;
m) animal, vegetable or synthetic glycerides;
n) animal, vegetable or synthetic waxes or chemically modified animal, vegetable waxes, such as beeswax, candelilla wax, carnauba wax, montan ester wax and rice germ oil wax, spermaceti, lanolin, jojoba wax, Sasol wax, Japan wax or Japan wax substitute;
o) animal and vegetable proteins, for example gelatin, gelatin derivatives, gelatin substitutes, casein, whey, keratin, soybean protein; zein and wheat protein;
p) mono- and disaccharides, oligosaccharides, polysaccharides, for example starches, modified starches and also pectins, alginates, chitosan, carrageenans;
q) vegetable oils, for example sunflower, thistle, cottonseed, soybean, corn germ, olive, rape (seed), linseed, olive tree, coconut, palm kernel oil and palm oil;
r) synthetic or semisynthetic oils, for example medium-chain triglycerides or mineral oils;
s) animal oils, for example herring, sardine and whale oils;
t) hardened (hydrogenated or partially hydrogenated) oils/glycerides, for example of the abovementioned oils, in particular hydrogenated palm oil, hydrogenated cottonseed oil, hydrogenated soybean oil;
u) varnish coatings, for example terpenes, in particular shellac, Tolu balsam, Peru balsam, sandarac and silicone resins;
v) fatty acids, both saturated and monounsaturated and polyunsaturated C6 to C24 carboxylic acids;
w) silicas.

Said coating materials can also be used in mixtures with one another.

Examples of suitable polyalkylene glycols a) are: polypropylene glycols and, in particular polyethylene glycols of different molar masses, for example PEG 4000 or PEG 6000, obtainable from BASF AG under the trade names Lutrol E 4000 and Lutrol E 6000.

Examples of above polymers b) are: polyethylene oxides and polypropylene oxides, ethylene oxide/propylene oxide mixed polymers and block copolymers made up of polyethylene oxide and polypropylene oxide blocks, for example polymers which are obtainable from BASF AG under the trade names Lutrol F68 and Lutrol F127.

Preferably, highly concentrated solutions of polymers a) and b) of up to about 50% by weight, for example from about 30 to 50% by weight, based on the total weight of the solution, can advantageously be used.

Examples of above polymers d) are: polyvinylpyrrolidones, as are distributed, for example, by BASF AG under the trade name Kollidon or Luviskol. Highly concentrated solutions of these polymers having a solids content of from about 30 to 40% by weight, based on the total weight of the solution, can advantageously be used.

An example of abovementioned polymers e) is: a vinylpyrrolidone/vinyl acetate copolymer which is distributed by BASF AG under the trade name Kollidon VA64 or Kollicoat SR. Highly concentrated solutions of these copolymers of from about 30 to 40% by weight, based on the total weight of the solution, can particularly advantageously be used.

Examples of above polymers f) are: products as are distributed, for example, by the Hoechst company under the trade name Mowiol. Solutions of these polymers having a solids content in the range from about 8 to 20% by weight can advantageously be used.

Examples of suitable polymers g) are: hydroxypropyl methyl celluloses, as are distributed, for example, by Shin Etsu under the trade name Pharmacoat.

Examples of abovementioned polymers h) are: alkyl (meth)acrylate polymers and copolymers, the alkyl group of which has from 1 to 4 carbons. Specific examples of suitable copolymers are: ethyl acrylate/methyl methacrylate copolymers which are distributed, for example, under the trade names Kollicoat EMM 30D by BASF AG, or under the trade name Eutragit NE 30 D by the Rö company; and also methacrylate/ethyl acrylate copolymers, as are distributed, for example, under the trade name Kollicoat MAE 30DP by BASF AG or under the trade name Eutragit 30/55 by the Rö company. Such copolymers can be processed, for example, as from 10 to 40% strength by weight dispersions according to the invention.

Examples of above polymers i) are: polyvinyl acetate dispersions which are stabilized with polyvinylpyrrolidone and are distributed, for example, under the trade name Kollicoat SR 30D by BASF AG (solids content of the dispersion from about 20 to 30% by weight).

Fats, for example those of animal, vegetable or synthetic origin; examples of animal fats m) are fats of pig, cattle and geese, a suitable fat is, for example, beef tallow. A suitable beef tallow is obtainable under the trade name Edenor NHIT-G (CAS No. 67701-27-3) from Cognis.

Other coating materials are gelatin, for example from cattle, pig, fish.

Other coating materials are waxes, for example vegetable waxes, for example candelilla wax, carnauba wax, rice germ oil wax, Japan wax or Japan wax substitute (obtainable under the trade name Japanwachsersatz [Japan wax substitute] 2909, Kahl Wachsraffinerie) etc.; synthetic waxes, such as cetyl palmitate (obtainable under the trade name Cutina CP, CAS 95912-87-1 from Cognis), animal waxes, for example lanolin, beeswax, shellac wax, spermacetti and chemically modified waxes such as jojoba wax, Sasol wax, montan ester wax.

In principle, other coatings from the solution are also conceivable: for example sugar coating.

Likewise, vegetable oils q) can be used, for example sunflower, thistle, cottonseed, soybean, corn germ and olive oils, rapeseed, linseed, olive tree, coconut, (oil) palm kernel and (oil) palm oils. Suitable palm oils are, for example, obtainable under the trade name Vegeol PR 265 from the Aarhus Oliefabrik company. Suitable rapeseed oils are obtainable under the trade name Vegeol PR 267 from the Aarhus Oliefabrik company. Palm kernel oil is obtainable under the trade name Tefacid Palmic 90 (CAS No. 57-10-3) from the Karlshamns company.

Likewise, use can be made of semisynthetic oils r), for example medium-chain triglycerides or mineral oils and/or animal oils s), for example herring, sardine and whale oils.

In a preferred embodiment, the coating materials used are hydrogenated vegetable oils t) including triglycerides, for example hydrogenated cottonseed oil, corn oil, peanut oil, soybean oil, palm oil, palm kernel oil, babassu oil, sunflower oil and safflower oil. Preferred hydrogenated vegetable oils comprise hydrogenated palm oil, cottonseed oil and soybean oil. The most preferred hydrogenated vegetable oil is hydrogenated soybean oil. Other fats and waxes originating from plants and animals are likewise suitable.

The hydrogenated vegetable oils preferably used can be in various polymorphous forms, these are the α, β and β' form. In a particularly preferred embodiment of the present invention, hydrogenated vegetable oils are used which are primarily in the β and β' form, in particular those which are predominantly in the β form. The term "predominantly" means that at least 25%, in particular at least 50%, preferably at least 75%, of the crystals are in the preferred polymorphous form.

Particular preference is given to the use of hydrogenated soybean oil having a content of greater than 50%, in particular greater than 75%, preferably greater than 90%, β and/or β' form.

For coating, use can be made of, for example, a liquid which is as highly concentrated as possible, but still sprayable, for example an up to 50% strength by weight aqueous or nonaqueous solution or dispersion of one or more of said coating materials. Likewise, pulverulent coating materials can be used.

Preferred coating materials comprise hydrogenated vegetable oils including triglycerides, for example hydrogenated cottonseed, corn, peanut, soybean, palm, palm kernel, babassu, sunflower and safflower oils. Preferred hydrogenated vegetable oils comprise hydrogenated palm oil, cottonseed oil and soybean oil. The most preferred hydrogenated vegetable oil is hydrogenated soybean oil. Other fats and wax originating from plants and animals are likewise suitable.

Other Substances (E)

In a further embodiment of the invention, the adsorbates can comprise other substances, examples being antioxidants, preservatives, binders and/or flavorings.

Antioxidants are advantageous, for example to protect the double bonds of the fatty acids from oxidation. However, the general health-promoting action of antioxidants is also known. Thus, in animal nutrition, use is made as antioxidants preferably of ethoxyquin, ascorbic acid, tertiary butylated hydroxytoluene, tertiary butylated hydroxyanisole, ascorbyl palmitate; apart from these, gamma- and alpha-tocopherols, tocotrienol, rosemary extract, isoflavones and carotenoids and naturally occurring polyphenols, for example flavonoids are also used.

In a preferred embodiment of the invention, the further substances (E) used are antioxidants if the components to be adsorbed (A) are oil-soluble compounds. In particular, if the components to be adsorbed are oil-soluble vitamins and/or unsaturated fatty acids.

In a preferred embodiment of the invention, use is made of antioxidants as further substances (E) if, as stabilizer (B), a compound of the group of the glycerides (b-1) is used.

The inventive formulation can comprise from 0.05 to 10% by weight of antioxidants. Preferably, it comprises 0.1 to 6% by weight of antioxidants, based on the components to be adsorbed (A).

The inventive formulation can also contain binders. Examples of suitable binders are: solutions of carbohydrates, for example glucose, sucrose, dextrins and the like, sugar alcohols, for example mannitol, or polymer solutions, for example solutions of hydroxypropyl methyl cellulose (HPMC), polyvinylpyrrolidone (PVP), ethoxylated cellulose (EC), ethyl cellulose or propyl cellulose. The binder content, based on the dry weight of the pulverulent formulation, can be, for example, in the range from about 0 to 20% by weight, for example from 1 to 6% by weight, based on the components to be adsorbed (A) depending on the type and adhesion properties of the binder used. For the binding, in the simplest case, heat can also be used.

Production of the Adsorbates

The adsorbates can be produced, for example, as follows: one or more carriers (C) are placed in a mixer or a fluidized-bed reactor and the components to be adsorbed (A) and if appropriate other substances (E) can be added. In rare cases the use of stirred fixed beds or moving beds is conceivable.

In principle, the components (A), (B), (C) and also other substances (E) can be combined in all conceivable combinations and sequences. The person skilled in the art will select this as a function of said components.

In a preferred embodiment, the component to be adsorbed (A) is mixed with a stabilizer (B) and then applied to the carrier (C). It is likewise possible to introduce first the carrier (C) and to add the components (A) and (B) either separately or premixed.

Mixing (A) and (B)

(A) and (B) can be mixed by customary methods depending on the physical state of (A) and (B). Both (A) and (B) can be in solid or liquid form. They can be dissolved or dispersed in suitable oils or in water or other solvents.

In the simplest case two liquids are mixed, it is equally conceivable that the stabilizer (B) is melted, the components to be adsorbed (A) are dissolved therein and the mixture, after adsorption to carrier (C), solidifies with cooling. It is likewise conceivable to melt (A) and (B), separately or together, to mix the melts homogeneously, to add the mixture to the carrier (C) and subsequently solidify it. Particular preference is given to mixing methods which lead to a uniform distribution of (A) in (B); these include homogeneous melts, solutions, or else dispersions.

The equipment required for this is known to those skilled in the art, that is to say heatable apparatuses which are preferably provided with mixing tools, for example agitators. The required energy input can result, for example, from heatable vessel walls, heatable mixing tools and/or mechanical energy input.

It is also possible to heat a component which is already liquid to the point that, after addition of the second as yet unmelted component in the desired concentration, both substances are then in the liquid state.

It is also conceivable first to disperse the still-solid substance in the liquid component via input of mechanical energy, and to heat both together further in apparatuses mentioned above.

If (B) is solid having highly varied particle size distributions, or (aqueous) solutions or dispersions alone, or together with other substances, it is advantageous to add (B) to (A), with or without water in the desired concentrations, and produce a dispersion therefrom.

If (B) is a pulverulent solid and (A) is in the form of a liquid, it is advantageous to stir (B) into (A) and to achieve a desired solidification, for example by lowering the mixture temperature.

In a further embodiment, (A) can be dispersed in an aqueous protecting colloid (for example gelatin)/sugar phase with addition of (B) with or without other additives. The solidification can be performed here again by lowering the temperature and/or by removal of water.

It is further conceivable to melt (A) or (B) or mixtures of (A) and (B), for example, by direct introduction of a third component, for example steam or heated water or other media.

(A) and (B) can be mixed (simultaneously with, or downstream of, heating) gently, or under intensive energy input.

In some cases, sufficient mixing is achieved alone as a result of molecular motion and density differences after a sufficiently long time, or via slow stirring or folding. If necessary, intensive agitation can be employed using optimized geometry and high-speed agitating or mixing elements.

In some cases a rotary motion or shaking motion of the complete apparatuses is sufficient in itself. In other cases, the necessary energy input for mixing is achieved via pumping the substances through static mixers, blending, or via other dispersion machinery. The energy input can also be achieved, for example, via ultrasonicating.

In a preferred embodiment, the stabilizer (B) is mixed with the carrier (C) and then applied to the component to be adsorbed (A).

Adsorbate Production: Application of (A), Preferably Mixed with (B), to (C) in a Mixer Batch or continuous mixers can be used. The carrier (C) is introduced with or without other additives. Plowshares, blades, screws or the like ensure product mixing which is intensive to a greater or lesser extent. Classic examples are plowshare mixers, conical screw mixers or similar apparatuses.

Mixing processes and mixers are described, for example, in technical information from Degussa(-Hüls), TI 1213,"Kieselsäuren als Fließhilfsmittel und als Trägersubstanz-Geeignete Mischverfahren für Pulver und Granulate" [Silicas as anticaking agents and as carrier substance-suitable mixing processes for powders and granules.]

Very flat, box-shaped or trough-shaped structures having one or more screws are also usable. Other structures are high-speed mixers, for example the Turbolizer® mixer/coater from Hosokawa Micron B.V.

Preferably, batch mixers can be used. The carrier material is charged with or without additives. Plowshares, blades, screws or the like ensure product mixing is intensive to a greater or lesser extent. Classic examples are plowshare mixers, conical screw mixers or similar apparatuses. Alternatively, product mixing via agitation of the entire vessel is possible. Examples of this are tumble mixers, drum mixers or the like. Another possibility is the use of pneumatic mixers (see Ullmann's Encyclopedia of Industrial Chemistry, Sixth Edition, Mixing of Solids).

The component to be adsorbed (A), in a preferred embodiment mixed with stabilizer (B), is metered/added, if appropriate together with other substances (E), generally via devices for sprinkling or spraying. Examples of these are lances, sprayheads, single-fluid or multi-fluid nozzles, in rare cases rotating sprinkling or atomization devices. In the simplest case, addition locally as a concentrated jet is also possible. Alternatively, the component to be adsorbed (A), in a preferred embodiment mixed with stabilizer (B), can first be placed in a mixer, in order then for the carrier (C) to be added.

The component to be adsorbed (A), preferably mixed with stabilizer (B), can be added at superatmospheric pressure, atmospheric pressure or reduced pressure compared with atmospheric pressure, preferably at atmospheric pressure and reduced pressure.

In isolated cases, it can be advantageous to preheat the component to be adsorbed (A) (decrease in viscosity, change in wetting properties), and also to supply or remove heat via the vessel wall and/or the mixing tools. In isolated cases it can be necessary to remove water vapor or solvent vapor. This is of interest, in particular, when the components to be adsorbed (A) are mixed with stabilizer (B).

Depending on the component to be adsorbed (A), those skilled in the art will preferably select the stabilizer or stabilizers in such a manner that a homogeneous mixture of (A) and (B) can be produced, this can also be in the form of a dispersion, for example.

The adsorbates are generally produced at temperatures which are above the melting point of the mixtures.

(B) is generally selected in such a manner that the mixture of (B) with the components to be adsorbed (A) is solid and homogeneous at temperatures below 80° C., preferably below 60° C., in particular below 40° C.

To increase the loading of the carrier (C) and to minimize oxygen inclusions, it can be expedient to evacuate the mixer containing the carrier before feed of the active compound, and also if appropriate to blanket it with protecting gas. Depending on the carrier, this is to be repeated several times.

Alternatively, continuous mixers are suitable. The components to be adsorbed (A), preferably mixed with (B), and any other substances (E) present and carrier (C) are preferably added in this case at different points in the mixer.

Adsorbates can be produced batchwise or continuously in the fluidized beds. The carrier (C) is agitated via the fluidizing gas, which may be hot. Air or else inert gas is suitable as fluidizing gas. In isolated cases it is expedient to supply or remove heat via the vessel wall and/or via heat exchanger surfaces immersed in the fluidized bed. Suitable fluidized beds and the peripheral equipment required are part of the prior art.

The components to be adsorbed (A), preferably mixed with (B), are metered and, if appropriate, preheated, batchwise or continuously by means of the abovedescribed devices which are known to those skilled in the art.

In isolated cases, adsorbates can advantageously be produced by means of a combination of mixer and fluidized bed.

If the adsorbates comprise further substances (E), these can be added together to components (A) and/or mixed with the carrier (C).

In isolated cases it can be advantageous, during the production of adsorbates in a mixer, or immediately thereafter/before, to add powdering agents such as talc, silicates or the like, to avoid agglutination.

If (B) is selected from the group (b-1) and/or (b-2), it is advantageous to mix (A) with (B) (for example by melting) and then apply the mixture to (C).

Particularly preferably, the mixture of (A) and (B) is to be fixed in, or in part on, (C) by temperature decrease, for example. It is advantageous, by selecting suitable temperatures, to lower the viscosity of the mixture of (A) and (B) to the extent that a sufficiently rapid and sufficiently complete loading of the carrier (C) can be achieved. This process is particularly advantageous if (B) comprises at least one compound from (b-1) and at least one compound from (b-2).

The mixture of (A) and (B) can be heated, for example, in upstream separate vessels or apparatuses or heatable piping. The carrier (C) can, if necessary, likewise be added preheated. The mixture of (A) and (B) and of (C) can be heated together or separately or else in the mixer itself. The heating can be performed by heat exchange via the vessel wall or heated mixing elements or via the input of mechanical stirring or mixing energy.

The mixture can be cooled again in the mixer itself by heat exchange via the vessel wall or coolable mixing elements or, in rare cases, by utilizing evaporative cooling. Obviously, cooling in downstream apparatuses or, in the simplest case, by heat exchange with the environment during storage is also possible.

If the stabilizers (B) used are compounds from the class of the emulsifiers (b-2), it has proven advantageous, for preparation of the mixture of (A) and (b-2), and if appropriate other stabilizers, to use one of the following processes:
- (a) Production of a mixture of emulsifier (b-2) and (A) with or without water and addition of this mixture to the carrier (C) placed in the mixer
- (b) Applying a, preferably water-free, emulsifier b-2, or an aqueous emulsifier solution or dispersion to the carrier (C) in the mixer with subsequent addition of (A) to the carrier thus already containing the stabilizer b-2
- (c) Combining (a) and (b) in any sequence If required, the individual components, (A), mixtures of (A) and (B), (C), or mixtures of (B) and (C) are heated and cooled as required.

Said processes have also proved particularly advantageous if the stabilizer (B) is selected from the group consisting of the polysaccharides (b-3).

In isolated cases, it may be necessary during production of the adsorbates to remove water vapor or solvent vapor. This can take place in the mixer itself via associated filters or in downstream apparatuses, for example in further dryers, mixers, stirred tanks, fluidized beds, spray dryers, prilling towers, etc., preferably under reduced pressure or atmospheric pressure.

In a further embodiment of the invention, the adsorbates are coated after their production. This can be carried out directly in the mixer or in downstream apparatuses. This can be performed by adding liquid coating materials as described under (D), or by adding initially solid coating material (D) which melts or softens as a result of heating the wall of the apparatus or the shaft or as a result of mechanical energy input, and covers the adsorbate.

In a further embodiment, the adsorbate and the preferably pulverulent coating material (D) can be placed in the mixer, if appropriate premixed and the adsorbate is thus coated as a result of high mechanical energy input in the same or in separate apparatuses (examples are all previously mentioned mixers, but also slow grinders and dryers).

In isolated cases, it can be advantageous to preheat or cool (change of viscosity, change in wetting properties, effect on solidification properties) adsorbate and/or coating material (D) and also to supply or remove heat via the vessel wall and/or the mixing tools. In isolated cases it may be necessary to remove water vapor or solvent vapor. Wetting properties can also be changed by the addition of surface-active substances.

The application of coating materials serves for additional protection of the active compound, delaying or accelerating the release of active compound, amplification of the mechanism of action, or achieving additive effects.

The invention encompasses, during application of the coating material or immediately thereafter/before, the fact that powdering material such as talc, silicates or the like can be added to avoid caking.

Adsorbate Production: Application of (A), Preferably in a Mixture with (B), to (C) in the Fluidized Bed In a further embodiment of the invention, the adsorbates can be produced batchwise or continuously in fluidized beds. The particles are agitated by the fluidizing gas which is hot or chilled. Suitable fluidizing gases are, for example, air, or else inert gas (e.g. nitrogen). In isolated cases it is expedient to supply or remove heat via the vessel wall and also via heat-exchange surfaces immersed in the fluidized bed. Suitable fluidized beds and also the peripherals required are described in the prior art.

The batchwise or continuous metering and if appropriate preheating of (A), preferably of mixtures of (A) and (B), with or without other substances (E) and also of additives is performed in a similar manner to the procedures described in the mixing.

For example, the carrier (C) can be charged in a fluidized bed. This is fluidized and, by spraying, sprinkling etc. an aqueous or nonaqueous solution or dispersion or a melt of (A), preferably a mixture of (A) and (B), is loaded with these in the desired concentration.

Internals known in the prior art have been found to be useful, which internals reinforce targeted mixing of the carrier (C) to be loaded. Examples of these are rotary displacement bodies, Wurster tubes, or else specially fabricated fluidized-bed gas distribution plate geometries (inclination and/or perforation of the gas-distribution plate) or reinforcing the specific solids motion by means of appropriately arranged nozzles, for example tangential single-fluid nozzles, or two-fluid or multiple-fluid nozzles.

In a further embodiment of the invention, the inventive adsorbates can be produced by combining mixer and fluidized bed.

Obviously, in fluidized beds also, the coating can be applied subsequently.

Adsorbates and their Use

The invention further comprises adsorbates which are obtainable according to the abovementioned processes. These adsorbates are distinguished by an increased stability of the components to be adsorbed (A) and at the same time are simple to produce on an industrial scale. They may therefore be used in a multiplicity of food applications, cosmetics preparations and animal feed preparations. They are usable, in particular, in complex matrices, for example premixes in the animal feed industry.

The inventive adsorbates, uncoated, generally have a loading [defined as % by weight of the components to be adsorbed (A) based on % by weight of carrier (C)] of from 0.01 to 10.0, in particular from 0.1 to 5.0, preferably from 0.5 to 2.5.

The inventive adsorbates, uncoated, generally have a total loading [defined as sum of percentages by weight of the components to be adsorbed (A) and stabilizers (B) based on % by weight of carrier (C)] of from 0.02 to 15.0; in particular from 0.05 to 10, in particular from 0.2 to 8.0; preferably from 0.2 to 5.0, particularly preferably from 0.5 to 2.5.

EXAMPLES

All data in % by weight
Abbreviations and commercial products used

| EQ | ethoxyquin |
| --- | --- |
| CLA-ME | conjugated linoleic acid methyl ester |
| Sipernat 22 ® | silica from Degussa |
| Tixosil 38 X ® | silica from Rhodia |
| N-Zorbit M | tapioca-based maltodextrin from National Starch |

Comparative Examples

C 1a: Loading Carrier Silica with CLA in the Fluidized Bed

A Niro-Aeromatic, type MP-1 laboratory fluidized bed was available for the experimental procedure. The charge vessel used was a plastic cone having a gas distribution plate diameter of 110 mm and a perforated plate having 8% free surface area.

The carrier material used was Tixosil 38 X, a silica from Rhodia. 323 g of this silica were heated in a drying cabinet to 70° C. in a glass beaker and then charged into the cone of the laboratory fluidized bed.

The silica charged in the fluidized bed was uniformly fluidized at an air flow rate of from 10 to 15 m$^3$/h and at a feed air temperature of from 45 to 50° C. The CLA methyl ester (396 g) was sprayed onto the charged silica at 1 bar spraying pressure via reduced-pressure intake in the top-spray process using a 1.0 mm two-fluid nozzle. The spraying time was approximately 26 min.

Readily flowable adsorbates were obtained at a drying loss of approximately 2%.

C 1b: Coating the Adsorbate Obtained in C 1a

The adsorbate obtainable from C 1a was coated with an aqueous gelatin-sugar dispersion in a second working step in the same laboratory fluidized bed. Glutardialdehyde was then sprayed on for crosslinking.

Comparative Example C 2a and C 2b Production of Adsorbates

Example C 2a 802 g of a silica carrier (Sipernat 22®, Degussa, drying loss 5.6%) were charged into a plowshare mixer (Loedige type M5 GR). A mixture of 810 g CLA methyl ester oil and 8.0 g of ethoxyquin were sprayed via a spray pistol in the course of 4 min with stirring at approximately 200 rpm. The mixture was then further stirred for 5 min at a stirrer speed of 345 rpm. A readily flowable powder was obtained, see the table for the composition.

Example C 2b

In the same mixer, under addition of CLA methyl ester oil to a silica carrier (Tixosil 38 X®), in the same procedure, readily flowable powders were produced.

| | | | Formula in % | | | |
| --- | --- | --- | --- | --- | --- | --- |
| Ex-ample | Loading | Carrier (C) silica | Silica | (A) CLA-ME | (E) EQ | Residual moisture |
| C2a | 1.07 | Sipernat 22 | 46.7 | 50.0 | 0.5 | 2.8 |
| C2b | 1.18 | Tixosil 38X | 44.1 | 52.0 | 0.5 | 3.4 |

Adsorbate retentions in a premix test (piglet feed)

The retentions were studied under the following experimental conditions: storage temperature 40° C., relative humidity 70%, storage site climatically controlled cabinet, packing means 25 ml penicillin glasses, open. Sample weight: amount of adsorbate corresponding to approximately 25 mg of pure CLA methyl ester or CLA ethyl ester. Piglet feed (meal) 5 g. Analysis time points, starting determination, 2- and 4-week values (HPLC, duplicate determination each time).

Procedure: Adsorbates containing CLA methyl ester or CLA ethyl ester are mixed with the piglet feed and stored open in a climatically controlled cabinet for a period of 4 weeks at a temperature of 40° C. and a relative humidity of 70%. After 2 and 4 weeks, the retention times based on the respective starting value are determined.

Assessment of the samples (2 weeks at 40° C./70% RH):
Retention >70% very good; retention 50-70% good, retention 30-50% acceptable The retention is defined as the content of active compound after 14 days compared with the initial content of active compound.

The stability of CLA-ME (components (A)) in the adsorbates produced under comparative examples C2a and C2b was determined in the premix test. The premix test gave the following retentions after 14 days:

| Example | Retention |
| --- | --- |
| C2a | 36% |
| C2b | 33% |

Examples According to the Invention

Examples 1a to 1g

Production of Stable Adsorbates using Stabilizers (B) from the Class of Glycerides (b-1)

The glycerides selected were first weighed out and heated to a temperature which is 20° C. above the respective melting temperature of the glyceride and thus completely melted. The desired amount of component (A), here CLA methyl ester oil stabilized with 1% ethoxyquin (component E), was heated to the same temperature in parallel. Both liquids were then combined in a glass beaker and dispersed using the U-Turrax at 5000 rpm for two minutes.

In parallel, 640 g of Tixosil 38 X®, Rhodia were charged into a plowshare mixer (Loedige type M5 GR).

With stirring at approximately 200 rpm, the prepared mixture of CLA methyl ester oil, ethoxyquin and glyceride was then sprayed on using a spray pistol. The mixture was then further stirred for 5 min at a stirrer speed of 345 rpm and the resultant stable adsorbates were then charged into a dish. In each case, powder was obtained having the following compositions:

| | | | Formula in % | | | |
|---|---|---|---|---|---|---|
| No. | Loading/ total loading | (B) Glyceride | (C) silica Tixosil 38X ™ | (A) CLA-ME incl.1% by wt. of EQ (E) | (B) Glyceride | Residual moisture |
| 1a | 0.9/1.4 | Cutina CP | 40.2 | 37.1 | 20.1 | 2.6 |
| 1b | 1.2/1.4 | Cutina CP | 40.2 | 47.2 | 10.1 | 2.5 |
| 1c | 0.9/1.4 | Precirol ATO 5 | 40.1 | 37.1 | 20.1 | 2.7 |
| 1d | 1.2/1.4 | Precirol ATO 5 | 40.2 | 47.3 | 10.1 | 2.4 |
| 1e | 0.9/1.4 | Biogapress | 40.1 | 37.1 | 20.1 | 2.7 |
| 1f | 1.2/1.4 | Biogapress | 40.2 | 47.2 | 10.1 | 2.5 |
| 1g | 0.9/1.4 | Vegeol PR-267 | 40.2 | 37.1 | 20.1 | 2.6 |

Retentions of the adsorbates as described in examples 1a to 1g in the premix test The premix test, after 14 days, gave the following retentions:

| Example | Retention |
|---|---|
| 1a | 69% |
| 1b | 64% |
| 1c | 61% |
| 1d | 71% |
| 1e | 58% |
| 1f | 67% |
| 1g | 61% |

Examples 2a to 2c

Production of Stable Adsorbates using Stabilizers (B) from the Class of the Emulsifiers (b-2)

640 g of Tixosil 38 X®, Rhodia, were first charged into a plowshare mixer (Loedige Type M5 GR).

In Example 2a, the desired amount of CLA methyl ester oil (component A), stabilized with 1% ethoxyquin (component E), was mixed with Cremophor CO 40 (component b-2) and predispersed using the U-Turrax for 30 seconds at 5000 rpm. The water was added and this mixture was emulsified using the U-Turrax for 10 minutes at 8800 rpm. This mixture was charged into a spray pistol and sprayed onto the silica charged in the mixer, with stirring. Apart from this, the procedure described in example 1 was followed.

In Example 2b, the Cremophor CO 40 was first mixed with water and this mixture was sprayed onto the silica. Not until then was the CLA methyl ester oil, stabilized with 1% ethoxyquin, sprayed onto the silica already precharged with emulsifier and water. Apart from this, the procedure described in example 2a was followed.

In Example 2c, the desired amount of CLA methyl ester oil, stabilized with 1% ethoxyquin, was mixed with Cremophor CO 40 and dispersed using the U-Turrax at 10 000 rpm for two minutes. In the absence of additional water, the emulsifier/CLA/EQ mixture was sprayed onto the silica using the spray pistol. Apart from this, the procedure described in example 2a was followed.

Adsorbates were obtained in each case having the following compositions:

| | | | Formula in % | | |
|---|---|---|---|---|---|
| Example | Loading/ total loading | (C) Tixosil 38X | (A) CLA-ME incl. EQ | (B) Cremophor CO 40 | Water |
| 2a | 1.19/1.28 | 40.0 | 48.4 | 2.9 | 8.7 |
| 2b | 1.19/1.28 | 40.0 | 48.4 | 2.9 | 8.7 |
| 2c | 1.33/1.43 | 40.0 | 54.1 | 2.9 | 3.0 |

Retentions of the Adsorbates from Examples 2a to 2c in the Premix Test

In the premix test, the above-cited stable adsorbates which were produced in the Lödige mixer were tested. The premix test gave the following retentions after 14 days:

| Example | Retention |
|---|---|
| 2a | 64% |
| 2b | 63% |
| 2c | 80% |

Example 3

Production of Stable Adsorbates using Stabilizers (B) from the Class of the Polysaccharides (b-3)

640 g of Tixosil 38 X®, Rhodia were first placed into a plowshare mixer (Loedige type M5 GR). CLA methyl ester oil, stabilized with 1% ethoxyquin, was heated in a glass beaker to 70° C. and the desired amount of N-Zorbit M was stirred in. This mixture was charged into a spray pistol and sprayed with stirring onto the silica introduced first into the mixer. Apart from this, the procedure as described in example 1a was followed.

A powder of the following composition was obtained:

| | | Formula in % | | |
|---|---|---|---|---|
| Example | (C) Tixosil 38X | (A) CLA-ME incl. EQ (E) | (B) N-Zorbit M | Water |
| 3 | 40.0 | 48.2 | 8.8 | 3.0 |

Retentions of the adsorbates as described in example 3 in the premix test (after 14 days)

| Example | Loading/ Total loading | Retention |
|---|---|---|
| 3 | 1.18/1.43 | 67% |

Examples 4a to 4c

Production of Adsorbates using Stabilizers (B) from the Class of the Chelators (b-4)

CLA methyl ester oil, stabilized with 1% ethoxyquin, was mixed in a first step with various chelators (b-4). If required, water and, additionally as stabilizer, the emulsifier (b-1) Cremophor CO 40 were added.

With the aid of these solutions or dispersions, again in a similar manner to example 1a, adsorbates of the following composition were produced in the Lödige mixer.

| | | Formula in % | | |
|---|---|---|---|---|
| Example | (C) Tixosil 38X | (A) CLA-ME incl. EQ (E) | Chelator (B) | Water |
| 4a | 39.9 | 54.1 | 2.9% salicylic acid | 3.1 |
| 4b | 40.1 | 54.2 | 2.9% stearyl citrate | 2.8 |
| 4c | 40.2 | 49.4 | 2.5% tartaric acid + 2.5% Cremophor CO 40 | 5.4 |

Retentions of Adsorbates 4a to 4b in the Premix Test
The premix test gave the following retentions after 14 days:

| Example | Loading/Total loading | Retention |
|---|---|---|
| 4a | 1.33/1.43 | 70% |
| 4b | 1.32/1.42 | 69% |
| 4c | 1.2/1.36 | 62% |

Example 5

Stabilized Adsorbates containing Vitamin E Acetate

Comparative experiment C5: Production of an unstabilized adsorbate containing vitamin E acetate In a first step, 816 g of vitamin E acetate (feed grade) were heated in a drying cabinet to 65° C. 800 g of a silica carrier material (Tixosil 38 X®, Rhodia) were placed in a plowshare mixer (Loedige type M5 GR).

With stirring at approximately 350 rpm, in a second step, the vitamin E acetate was sprayed onto the silica via a spray pistol in the course of 4 min. The mixture was then further stirred for 5 min at a stirrer speed of 600 rpm. A homogeneous, readily flowable powder of the following composition was obtained:

| | | Formula in % | | |
|---|---|---|---|---|
| Example | Silica | Silica | Vitamin E acetate | Residual moisture |
| C5 | Tixosil 38 X ® | 46.2 | 50.6 | 3.2 |

Examples 5a-c

Production of stable adsorbates containing vitamin E acetate, using stabilizers from the group of the emulsifiers (b-2)

800 g of Tixosil 38 X®, Rhodia, were first placed in a plowshare mixer (Loedige type M5 GR).

Example 5a

Cremophor™ GO 32 was used as emulsifier. In a first step, 816 g of vitamin E acetate (feed grade) and 40.8 g of Cremophor™ GO 32 were heated to 65° C. in seperate glass beakers in a drying cabinet, then mixed and dispersed using the U-Turrax for 60 seconds at 5500 rpm. This mixture was charged into a spray pistol and, with stirring, sprayed onto the silica introduced first in the mixer. Apart from this, the procedure as in comparative example C5 was followed.

Example 5b

Example 5b was carried out in a similar manner to example 5a, but instead of Cremophor™ GO 32, Cremophor™ GS 32 was used as emulsifier.

Example 5c

Cremophor GS 32 was used as emulsifier. In a first step, 816 g of vitamin E acetate (feed grade), 40.8 g of Cremophor GS 32 and 40.8 g of water were heated to 65° C. in separate glass beakers in a drying cabinet, then mixed and dispersed using the U-Turrax for 60 seconds at 5500 rpm. This mixture was charged into a spray pistol and, with stirring, sprayed onto the silica introduced first in the mixer. Apart from this, the procedure as described in example 5 was followed.

Example 5d

Production of a stable adsorbate containing vitamin E acetate, using a stabilizer from the group of the glycerides (b-1)

In a first step, 808 g of vitamin E acetate (feed grade) were heated to 80° C. in a drying cabinet. In parallel with this, 89.8 g of Vegeol PR-269 (50% Vegeol CO 52 S and 50% Palmowar FH) were heated to 80° C. in the drying cabinet and melted. Vegeol PR-269 was obtained from Aarhus Olie and has a melting point from 60 to 65° C. Both liquids were then poured together into a glass beaker and dispersed using the U-Turrax for two minutes at 5000 rpm.

702 g of a silica carrier material (Tixosil 38 X®, Rhodia) were placed in a plowshare mixer (Loedige type M5 GR).

With stirring at approximately 200 rpm, the prepared liquid mixture of vitamin E acetate (feed grade) and Vegeol PR-269 was then sprayed onto the silica using a heated spray pistol. The mixture was then further stirred for another 5 min and thereafter cooled in the mixer and discharge dish. A free-flowing powder was obtained.

The adsorbates produced as described in example 5 were studied for their stability in the standard premix test:

The standard premix test for vitamin E acetate was carried out under the following conditions: Storage temperature 40° C., relative humidity 70%, storage site climatically controlled cabinet, packing means PE film pouch, sealed.

Initial test charge 2 g of vitamin E acetate formulation (50% VEA), 200 g of premix (50% magnesium oxide, 45% fine lime, 5% trace elements)

Trace elements 46.78% $FeSO_4 \cdot 7\ H_2O$; 37.43% $CuSO_4 \cdot 5\ H_2O$; 11.76% ZnO; 3.61% MnO; 0.39% $CoCO_3$ Analysis times: Initial determination and 4 weekly values (HPLC, each in quadruplicate)

Procedure

The adsorbates under test (containing vitamin E acetate) were mixed well with the premix and stored at a temperature of 40° C. and a relative humidity of 70% for a period of, in total, 4 weeks in sealed PE film pouches. After 4 weeks, the retentions based on the respective starting value were determined.

Retentions of the examples C5 and also 5a to 5d in the standard premix test (4 weeks):

| Example | Retention |
|---------|-----------|
| C5 | 88% |
| 5a | 92% |
| 5b | 92% |
| 5c | 93% |
| 5d | 94% |

As the table shows, the inventively stabilized adsorbates exhibit a significantly higher retention of the active compound (vitamin E acetate) compared with the non-stabilized adsorbate (C5).

We claim:

1. A method for the production of a human or animal nutrition product comprising producing an adsorbate suitable for human or animal nutrition comprising applying a component to a carrier using at least one stabilizer such that the component is adsorbed to the carrier,
   wherein the carrier has a mean particle size of at least about 200 μm and is a silica or a silica derivative, and
   wherein the stabilizer is selected from the group consisting of
   1) a glyceride;
   2) an emulsifier selected from the group consisting of
      i) non-ionogenic surfactants from at least one of the following groups
         (1) addition products of from 2 to 30 mol of ethylene oxide and/or from 0 to 5 mol of propylene oxide to linear fatty alcohols containing from 8 to 22 carbons, to fatty acids containing from 12 to 22 carbons, and/or to alkylphenols containing from 8 to 15 carbons in the alkyl group;
         (2) $C_{12/18}$-fatty acid monoesters and diesters of addition products of from 1 to 30 mol of ethylene oxide to glycerol;
         (3) glycerol monoesters and diesters and/or sorbitan monoesters and diesters of saturated and unsaturated fatty acids containing from 6 to 22 carbons or their ethylene oxide addition products;
         (4) alkyl monoglycosides and oligoglycosides containing from 8 to 22 carbons in the alkyl radical and/or ethoxylated analogs thereof;
         (5) addition products of from 15 to 60 mol of ethylene oxide to castor oil and/or hardened castor oil;
         (6) polyol esters, polyglycerol esters, polyglycerol polyricinoleate, polyglycerol poly-12-hydroxystearate, polyglycerol dimerate, and/or mixtures thereof;
         (7) addition products of from 2 to 15 mol of ethylene oxide to castor oil and/or hardened castor oil;
         (8) partial esters based on unbranched, branched, unsaturated or saturated $C_{6/22}$-fatty acids, ricinoleic acid, 12-hydroxystearic acid, glycerol, polyglycerol, pentaerythritol, dipentaerythritol, sugar alcohols, alkyl glucosides, and/or polyglucosides;
         (9) mono-, di- and/or trialkyl phosphates, and/or mono-, di- and/or tri-PEG-alkyl phosphates and/or salts thereof;
         (10) lanolin alcohols;
         (11) polysiloxane-polyalkyl-polyether copolymers and/or corresponding derivatives;
         (12) mixed esters of pentaerythritol, fatty acids, citric acid and fatty alcohol and/or mixed esters of fatty acids containing from 6 to 22 carbons, methylglycose, and polyols; and/or
         (13) polyalkylene glycols;
      ii) a zwitterionic surfactant;
      iii) an ampholytic surfactant;
      iv) a quaternary emulsifier;
      v) a glycerophospholipid; and
      vi) a glyceroglycolipid;
   3) a polysaccharide; and
   4) a chelator;
   wherein the component is a conjugated fatty acid comprising at least 50% of one of 9-cis-, 11-trans-octadecadienoic acid or 10-trans-, 12-cis-octadecadienoic acid and wherein the adsorbate is coated.

2. The method of claim 1, wherein the component is mixed with the stabilizer prior to application to the carrier.

3. The method of claim 1, wherein the carrier comprises at least about 10% by weight of the adsorbate.

4. The method of claim 1, wherein the ratio of stabilizer to component is less than or equal to about 10.

5. The method of claim 1, wherein the ratio of stabilizer to component is less than or equal to about 1.

6. The method of claim 1, wherein the stabilizer comprises at least one glyceride and at least one emulsifier.

7. The method of claim 1, wherein the component is a conjugated octadecapolyenoic acid.

8. The method of claim 7, wherein the component is an octadecadienoic acid.

9. The method of claim 1, wherein the conjugated fatty acid comprises one or more conjugated octadecapolyenoic acids.

10. The method of claim 1, wherein less than about 5% of the fatty acid content is any one of or a combination of, 11,13-octadecadienoic acid isomers, 8,10-octadecadienoic acid isomers, cis-,cis-octadecadienoic acid isomers or trans-,trans-octadecadienoic acid isomers.

11. The method of claim 1, wherein the carrier is silica.

12. The method of claim 1, wherein the coating is selected from the group consisting of a polyalkylene glycol, a polyethylene glycol, a polyalkylene oxide polymer, a polyalkylene oxide copolymer, a block copolymer of polyoxyethylene and polyoxypropylene, a substituted polystyrene, a maleic acid derivative and a styrene-maleic acid copolymer, a polyvinylpyrrolidone, a vinylpyrrolidone/vinyl acetate copolymer, a polyvinyl alcohol, polyvinyl phthalate, hydroxypropylmethyl, a alkyl(meth)acrylate polymer or copolymer, an ethyl acrylate/methyl methacrylate copolymer, a methacrylate/ethyl acrylate copolymer, a polyvinyl acetate, a polyalkylenes, a polyethylene, a phenoxyacetic acid-formaldehyde resin, a cellulose derivative, ethyl cellulose, ethyl methyl cellulose, methyl cellulose, hydroxypropyl cellulose, hydroxypropyl methyl cellulose, carboxymethyl cellulose, cellulose acetate phthalate, an animal glyceride, a vegetable glyceride, a synthetic glyceride, an animal wax, a vegetable wax, a synthetic wax, a chemically modified animal wax, a chemically modified vegetable wax, beeswax, candelilla wax, carnauba wax, montan ester wax, rice germ oil wax, spermaceti, lanolin, jojoba wax, Sasol wax, Japan wax or Japan wax substitute, an animal protein, a vegetable protein, gelatin, a gelatin derivatives, a gelatin substitute, casein, whey, keratin, soybean protein, zein, wheat protein, a monosaccharide, a disaccharides, an oligosaccharide, a polysaccharide, a starch, a modified starch, pectin, alginate, chitosan, carrageenan, vegetable oil, sunflower oil, thistle oil, cottonseed oil, soybean oil, corn germ oil, olive oil, rape (seed) oil, linseed oil, olive tree oil, coconut oil, palm kernel oil and palm oil, synthetic oil, semisynthetic oil, medium-chain triglyceride oil, mineral oil, animal oil, herring oil, sardine oil and whale oil, hardened oils, glycerides, hydrogenated oil, varnish coating, terpenes, shellac, Tolu balsam, Peru balsam, sandarac, silicone resins, fatty acids, saturated fatty acids, monounsaturated fatty acids, polyunsaturated fatty acids, C6 to C24 carboxylic acids and a silica.

13. The method of claim 1, wherein the adsorbate comprises an additional substance selected from the group consisting of antioxidants, preservatives, binders and flavorings.

14. The method of claim 13, wherein the additional substance is applied with the component.

15. The method of claim 13, wherein the additional substance is mixed with the carrier.

16. A human or animal nutrition product comprising an adsorbate suitable for human or animal nutrition which is prepared by applying a component to a carrier using at least one stabilizer such that the component is adsorbed to the carrier,
  wherein the carrier has a mean particle size of at least about 200 µm and is a silica or a silica derivative, and
  wherein the stabilizer is selected from the group consisting of
  1) a glyceride;
  2) an emulsifier selected from the group consisting of
    i) non-ionogenic surfactants from at least one of the following groups
      (1) addition products of from 2 to 30 mol of ethylene oxide and/or from 0 to 5 mol of propylene oxide to linear fatty alcohols containing from 8 to 22 carbons, to fatty acids containing from 12 to 22 carbons, and/or to alkylphenols containing from 8 to 15 carbons in the alkyl group;
      (2) $C_{12/18}$-fatty acid monoesters and diesters of addition products of from 1 to 30 mol of ethylene oxide to glycerol;
      (3) glycerol monoesters and diesters and/or sorbitan monoesters and diesters of saturated and unsaturated fatty acids containing from 6 to 22 carbons or their ethylene oxide addition products;
      (4) alkyl monoglycosides and oligoglycosides containing from 8 to 22 carbons in the alkyl radical and/or ethoxylated analogs thereof;
      (5) addition products of from 15 to 60 mol of ethylene oxide to castor oil and/or hardened castor oil;
      (6) polyol esters, polyglycerol esters, polyglycerol polyricinoleate, polyglycerol poly-12-hydroxystearate, polyglycerol dimerate, and/or mixtures thereof;
      (7) addition products of from 2 to 15 mol of ethylene oxide to castor oil and/or hardened castor oil;
      (8) partial esters based on unbranched, branched, unsaturated or saturated $C_{6/22}$-fatty acids, ricinoleic acid, 12-hydroxystearic acid, glycerol, polyglycerol, pentaerythritol, dipentaerythritol, sugar alcohols, alkyl glucosides, and/or polyglucosides;
      (9) mono-, di- and/or trialkyl phosphates, and/or mono-, di- and/or tri-PEG-alkyl phosphates and/or salts thereof;
      (10) lanolin alcohols;
      (11) polysiloxane-polyalkyl-polyether copolymers and/or corresponding derivatives;
      (12) mixed esters of pentaerythritol, fatty acids, citric acid and fatty alcohol and/or mixed esters of fatty acids containing from 6 to 22 carbons, methylglycose, and polyols; and/or
      (13) polyalkylene glycols;
    ii) a zwitterionic surfactant;
    iii) an ampholytic surfactant;
    iv) a quaternary emulsifier;
    v) a glycerophospholipid; and
    vi) a glyceroglycolipid;
  3) a polysaccharide; and
  4) a chelator;
  wherein the component is a conjugated fatty acid comprising at least 50% of one of 9-cis-, 11-trans-octadecadienoic acid or 10-trans-, 12-cis-octadecadienoic acid and wherein the adsorbate is coated.

* * * * *